(12) United States Patent
Lee

(10) Patent No.: US 6,558,394 B2
(45) Date of Patent: May 6, 2003

(54) SURGICAL CAST CUTTER

(76) Inventor: Byung-Ho Lee, 1602-1503, Munchon-maeul Newsamik Apartment, 117, Juyeop-dong, Ilsan-gu, Goyang-city (KR)

( * ) Notice: Subject to any disclaimer, the term of this patent is extended or adjusted under 35 U.S.C. 154(b) by 82 days.

(21) Appl. No.: 09/823,742

(22) Filed: Mar. 30, 2001

(65) Prior Publication Data

US 2002/0038124 A1 Mar. 28, 2002

(30) Foreign Application Priority Data

Sep. 22, 2000 (KR) ......................................... 2000-55697
Sep. 22, 2000 (KR) ......................................... 2000-55698

(51) Int. Cl.[7] .............................. A61F 5/04; B27B 9/04
(52) U.S. Cl. ...................................... 606/105.5; 30/390
(58) Field of Search ............................. 606/105.5, 172, 606/180; 30/390; 602/9

(56) References Cited

U.S. PATENT DOCUMENTS

| | | | | |
|---|---|---|---|---|
| 983,368 A | * | 2/1911 | Holt ............................. | 30/390 |
| 2,366,017 A | * | 12/1944 | Fortune ........................ | 30/390 |
| 2,429,356 A | * | 10/1947 | Hicks ........................... | 30/390 |
| 2,490,878 A | * | 12/1949 | Marsh .......................... | 30/390 |
| 4,081,906 A | * | 4/1978 | Sigler ........................... | 30/390 |
| 4,421,111 A | * | 12/1983 | Rothman .................. | 606/105.5 |
| 4,611,585 A | * | 9/1986 | Steidle .................... | 606/105.5 |
| 4,829,993 A | * | 5/1989 | Silvey ............................ | 602/9 |
| 5,012,582 A | * | 5/1991 | Bristol et al. ................. | 30/390 |
| 5,020,226 A | * | 6/1991 | Chabbert ................. | 606/105.5 |
| 5,944,675 A | * | 8/1999 | Bequet-Sharber et al. ..... | 602/9 |
| 6,129,731 A | * | 10/2000 | Haeusier et al. ............ | 606/180 |

* cited by examiner

*Primary Examiner*—Todd E. Manahan
(74) *Attorney, Agent, or Firm*—GWiPS

(57) ABSTRACT

A surgical cast cutter for removing orthopedic bandages of a hard casting material type comprises a first shank (2a), cutting portion (2b), and second shank (2c); a first housing (1) having a built-in rotating device which rotates the cutting tool; a tool holding device which rotatably holds the cutting tool (2); a second housing (15) which receives the cutting tool (2) and having an integrated horseshoe-shaped protrusion which is inserted between the hard cover and affected area as a guide such that the hard cover may be easily cut; and a hood (50) which is coupled to the second housing (15) and movable in the up and down direction. The hood also serves as a collecting device for collecting dusts and debris formed from the removal of the cast. A method is also disclosed for applying the cast on an affected area such that it may be easily removed by the cast cutter.

6 Claims, 4 Drawing Sheets

SURGICAL CAST CUTTER

BACKGROUND OF THE INVENTION

1. Field of the Invention

This invention relates to a surgical instrument in particular to a cast cutter for removing orthopedic bandages of a hard-casting material type, and a method for casting the affected area in such a manner so that the cast may be easily cut by using the cast cutter.

2. Description of the Prior Art

Various devices and methods for removing a cast from an affected area of a patient have been developed. For example, an electric saw having a rotating or oscillating blade has been used to remove the cast from the affected area of a patient.

This electric saw has proved unsatisfactory for many reasons. In particular, this electric saw often shocks the patient getting the cast removed due to the approach of the rotating or oscillating blade against the affected area and the noise and debris generated when the electric-saw piercingly cuts the cast. This is particular disadvantage can especially occur when the patient is a child.

In addition, because of the above disadvantages, cast cuttings using an electric saw remove the cast from the affected area by penetrating through the cast in such a way so that the rotating or oscillating blade does not contact the affected area. This method necessitates the cutting of the cast once and then the use of a separate mechanical device for spreading the cut cast open.

The two separate actions must be performed due to the possibility of shock to the patient and because the operator must perform the task of cutting the cast with the electric saw, which requires extreme caution, twice on two uniform portions of the cast to avoid using a separate mechanical device to spread the cut cast open, causing agony for both the patient and the operator.

SUMMARY OF THE INVENTION

Therefore, the object of the present invention is to provide a cast cutter which does not cause shock or injury to the patient when removing the cast from the affected area, and which is provided with a hood which can be moved up and down according to the flexion caused from the difference in thickness of the cast. The hood also serves the additional role of collecting dust and debris formed from the removal of the cast.

Another object of the present invention is to provide a casting method whereby the cast cutter may perform the cutting operations easily when removing a cast from an affected area.

To achieve the above-mentioned objects, the cast cutter, according to this invention includes a cutting tool comprised of a first shank, cutting portion, and second shank; a first housing having a built-in rotating means which rotates the cutting tool; a tool holding means which rotatably holds the cutting tool; a second housing which receives the cutting tool having an integrated horseshoe-shaped protrusion which is inserted between the hard cover and affected area as a guide such that the hard cover may be easily cut; and a hood which is coupled to the second housing and which is movable in the up and down direction.

The method of cutting the cast by using the cast cutter configured as the above is comprised of the steps of wrapping a cast padding on the affected area; adhering adhesive tape of a smooth surfaced strip-shape on the cast padding under the hard cover portion to be cut when the hard cover is removed from the affected area with the hard cover cutter; and wrapping the hard cover on the cast padding on which the adhesive tape is adhered on a portion thereof.

BRIEF DESCRIPTION OF THE DRAWINGS

The preferred embodiments of this invention will now be described with reference to the attached figures wherein.

DETAILED DESCRIPTION OF THE PREFERRED EMBODIMENTS

Figure 1:
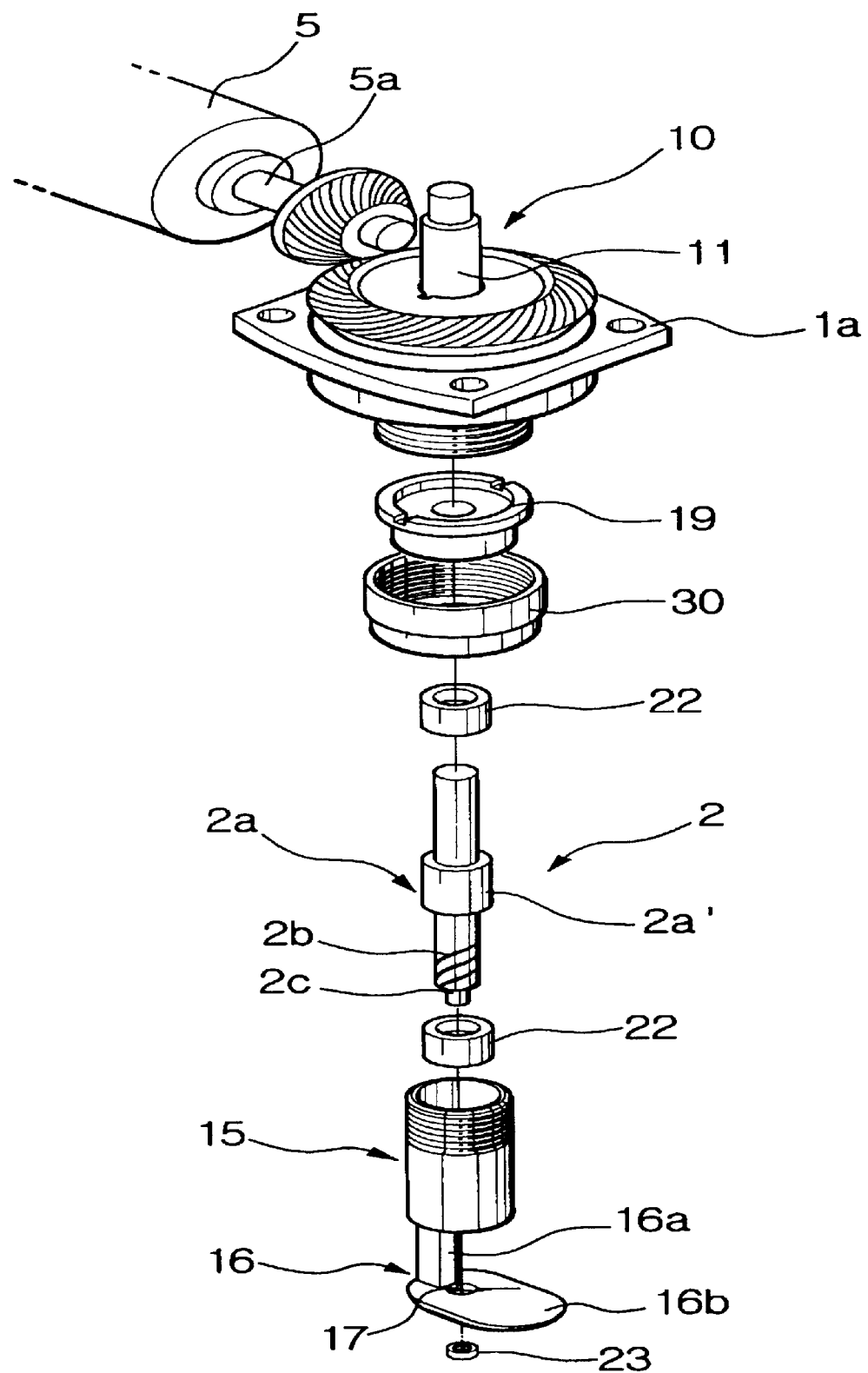
FIG. 1 is a perspective view of the main portion of the cast cutter according to this invention.
Figure 2:
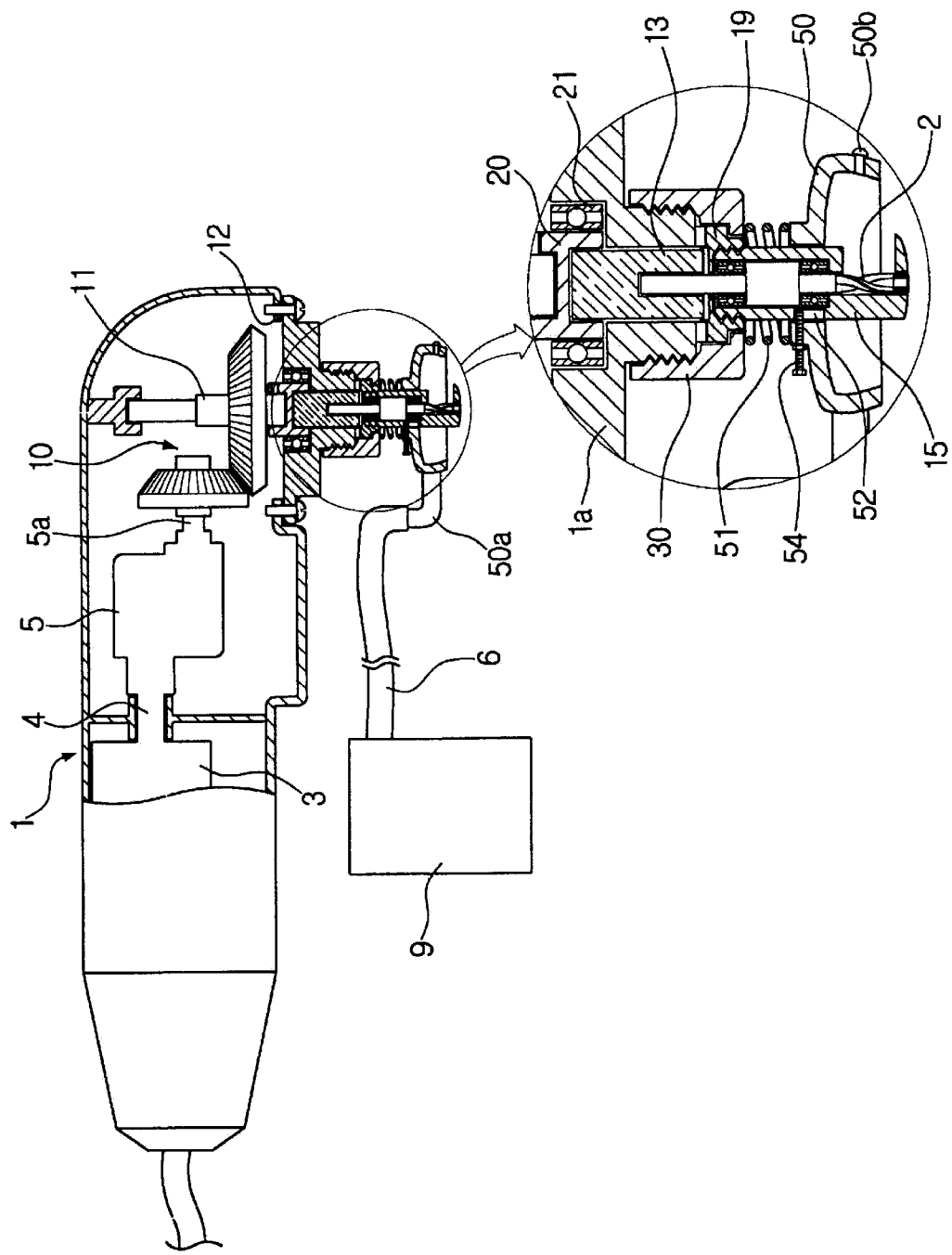
FIG. 2 is a cross-sectional view of a cast cutter provided with a dust collector hood.

A cast cutter having a first housing (1) extended longitudinally and having an opening (12) on the bottom of the front end thereof, and a cutting tool (2) mounted on the bottom of the front end of the first housing (1) perpendicular to the direction of the longitudinal axis of the first housing (1) is depicted in FIGS. 1 and 2.

A stop plate (1a) which closes opening (12) being formed on the bottom of the front end of the first housing (1) holds the mounted cutting tool (2) such that it may be rotationally driven by motor (3).

The front axle (4) of the motor (3) extends to the front end side of the housing (1), and a transmission (5) connected thereto to convey the dynamic power of the motor (3) to a set of bevel gears (10) in predetermined revolutions the transmission (5) is connected to a set of bevel gears (10) to convert the rotation centered on a first output axle (5a) parallel to the front axle (4) to a rotation centered on a second output axle (11) perpendicular to the first output axle (5a).

As depicted in FIG. 2, the bevel gear (10) of the output side which the second output axle (11) is passed through integrally has on the output side a cylindrical portion (20) with a H-shape cross-section coupled to the second output axle (11) in a key connection. Therefore, the cylindrical portion (20) rotates in the same revolutions as the second output axle (11).

The cylindrical portion (20) has a interposing first bearing (21) rotatably mounted on the stop plate (1a) which closes the opening (12) formed on the bottom of the front end of the first housing (1), as shown in FIG. 2. Therefore, the third output axle (13) rotates in same revolutions as the cylindrical portion (20).

The cutting tool (2) is comprised of a first shank (2a), a cutting portion (2b), and a second shank (2c), as shown in FIG. 1, and the proximal end portion of the first shank (2a) is coupled to the third output axle (13) in the key connection manner. Therefore, the cutting tool (2) rotates in same revolutions as the third output axle (13).

As depicted in FIG. 1, the first shank (2a) of the cutting tool (2) has a stopper (2a') formed on the center thereof, the cutting portion (2b) of the cutting tool (2) has cutting blades (for example, two or three cutting blades) formed in spiral shape, and the second shank (2c) of the cutting tool (2) has a diameter smaller than that of the cutting portion (2b).

The first shank (2a), excluding the proximal end portion of the cutting tool (2), respectively has second bearings (22,22) interposed on the circumference of the top and bottom portions where it contacts the stopper (2a') and the second housing (15) is rotatably inserted and mounted.

The distal end of the second housing (15) has a horseshoe-shaped protrusion (16) formed thereon which serves as a cutting guide for the cutting tool (2), the horseshoe-shaped protrusion (16) is comprised of a first portion (16a) extended parallel to the cutting tool, and a second portion (16b) integrally connected to the distal end of the first portion (16a) extending from the distal end of the first portion in the perpendicular direction of the cutting tool (2).

On the second portion (16b) there is formed a second opening (17), and in the second opening (17) the second shank (2c) of the cutting tool (2) interposes a third bearing (23) and is inserted therein. In addition, the second portion (16b) has a plate shape, the thickness of which decreases from the distal end to the proximal end and from the center portion to both ends.

The second housing (15), which has threads formed on the upper portion of the outer surface, is joined together with the cascaded first joint (19) through which the first shank (2a) of the cutting tool (2) is passed through, as depicted in FIG. 2, the first joint (19) is coupled to the stop plate (1a) at the upper portion. In addition, the first joint (19) is inserted into a second joint (30) which has a cascaded shape corresponding to that of the first joint (19) in the inner surface thereof, the second joint (30) is coupled to the stop plate (1a) of the first housing (1) as shown in FIG. 2.

The second housing (15) has adhered on the outer surface thereof in a key connection, a hood (50) connected to a duct channel (6), which suctions and guides debris generated during cast cutting through the rotation of a impeller mounted on a separate motor other than the motor (3) mounted on the cast cutter. Here, the duct channel (6) is connected to a collection chamber (9) installed separately from the cast cutter.

Between the hood (50) and the second joint (30) there is interposed a spring (51), on a portion of the outer surface of the second housing (15) there is formed a long slot-type groove (52) in the longitudinal direction of the second housing (15), on a location of the hood (50) corresponding to the slot-type groove (52) there is formed a threaded aperture, and bolt (54) passes through the aperture and is inserted into the slot-type groove (52) coupling the hood (50) and the second housing (15).

Therefore, through the above configuration, the hood (50) may be resiliently moved up and down along the slot-type groove (52) and thereby the cast cutter is not interfered by the curves of the cast caused from the varying thickness of the cast when advancing for the cast cutting operation.

The hood (50) may be formed of a light transparent material to display the state of the debris of the cast being suctioned into the collection chamber (9), and to be connected to the duct channel (6), where there is formed on the proximal end of the cast cutting direction an angled nipple-type connector (50a), and on the distal end there is formed a display (50b) showing the cast cutting direction.

In addition, the outer surface of the hood (50) is formed of a smooth surface to facilitate the cast cutting operations, and all edges are rounded.

The operation of the cast cutter is now described.

The motor (3), which is connected to a power source (not shown), drives the front axle (4), the front axle (4) rotates the first output axle (5a) in predetermined revolutions through the transmission (5). Then, one of the bevel gears, among the set of bevel gears (10), mounted on the first output axle (5a) in a key connection manner rotates in the revolutions of the first output axle (5a), the other bevel gear, which is meshed in a ninety degree angle with the one of the bevel gears, rotates with a output axle (11) disposed forming a ninety degree angle with the first output axle (5a).

When the output axle (11) rotates, the cylindrical portion (20), which mounts the output axle (11) on one side in a key connection, rotates and accordingly the third output axle (13), which is connected in a key connection manner, rotates.

Then the cutting tool (2), which is connected in key connection with the third output axle (13), is rotated. Here, the second portion (16b) of the second housing (15) is inserted between the normal cast padding wrapped around the affected area and the hard cover wrapping around the normal cast padding, and the cast cutter is advanced. The hard cover is cut by the cutting tool (2) consequent to the advancement thereof.

When the hard cover is cut by the cutting tool (2), the debris from the hard cover is collected in the collection chamber (9) through the hood (50) and duct channel (6).

The preferred embodiments of the method of casting the affected area such that the cast may be easily cut by the cast cutter according to the present invention will be described hereinafter.

The method according to this invention is a casting method which allows smooth movement of the horseshoe-shaped protrusion of the second housing, which serves as a guide for the hard cover cutter, when in between the hard cover and the cast padding during the cast removal process.

Figure 3:
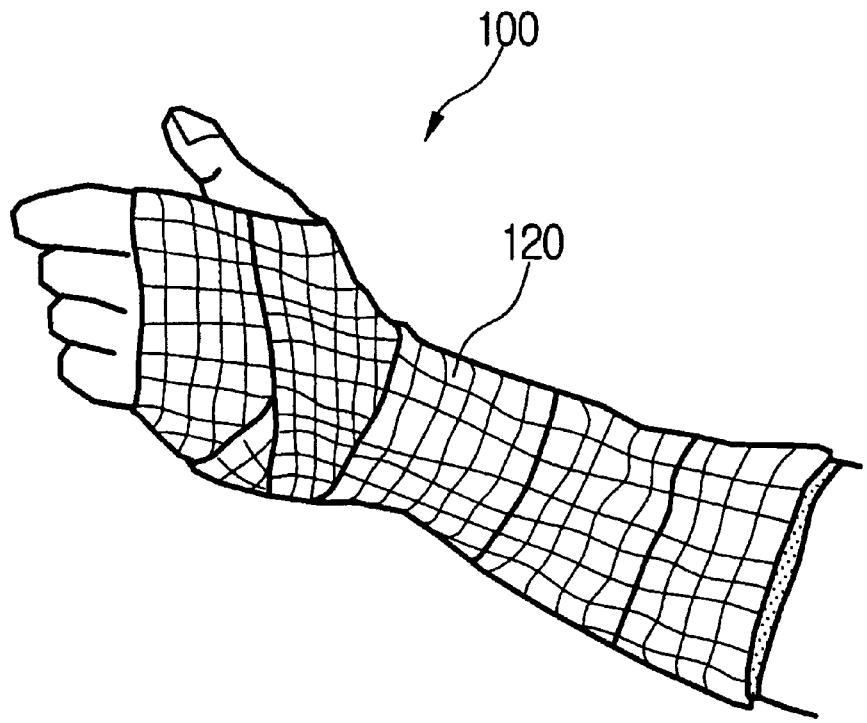
FIG. 3 is a perspective view of an affected area wrapped with cast padding.

FIG. 3 depicts an affected area (arm)(100) of a patient wrapped in soft, light cast padding (120).

Figure 4:
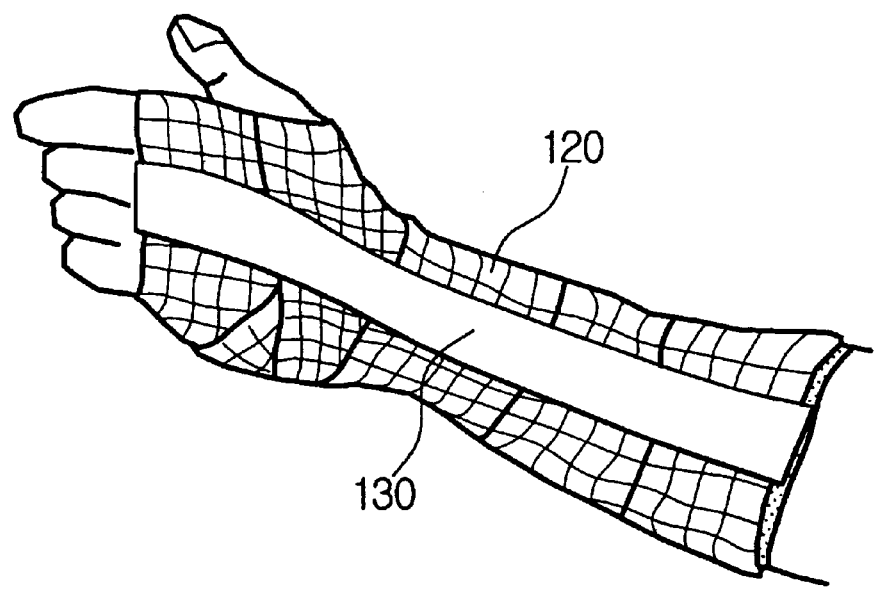
FIG. 4 is a perspective view of adhesive tape adhered to a portion of the cast padding of FIG. 3.

As in the state depicted in FIG. 3, on the cast padding (120) smooth surfaced, light, strip shaped adhesive tape (130) is adhered, as shown in FIG. 4, on the portion where the horseshoe shaped protrusion (210), which serves as a cutting tool guide for the hard cover cutter (200), which will be described hereinafter is moved.

Figure 5:
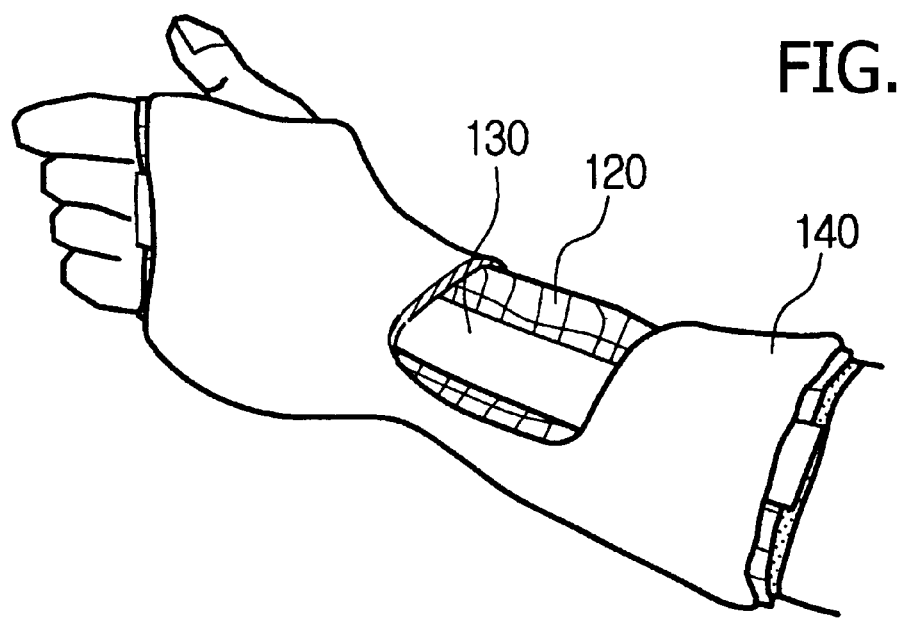
FIG. 5 is a perspective view of a hard cover wrapped on the cast padding of FIG. 4 onto which adhesive tape is adhered.

As depicted in FIG. 5, the cast padding (120), on which the adhesive tape (130) is adhered onto the portion where the horseshoe shaped protrusion (210) of the hard cover cutter (200) is to be moved, is wrapped by the hard cover (140). The hard cover may be, for example, plaster bandages, polyethylene resin and the like.

Figure 6:
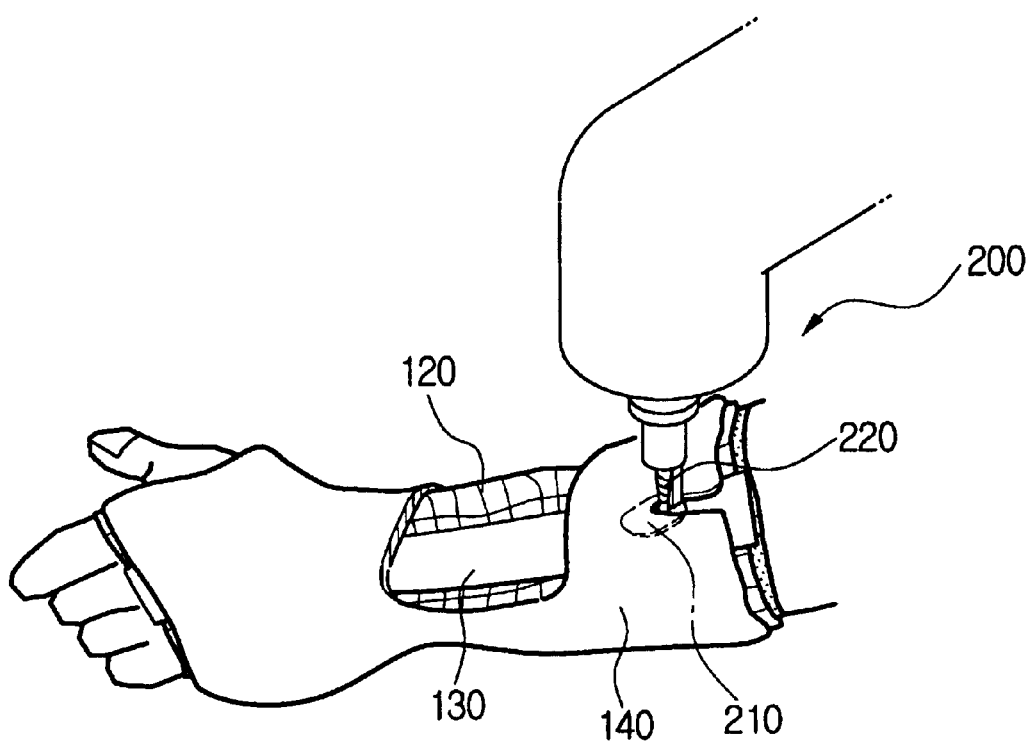
FIG. 6 is a perspective view of the cast cutter of this invention applied to the cast formed as FIG. 5.

FIG. 6 depicts the hard cover cutter (200) applied to the cast formed on the affected area through the method described above.

As shown in FIG. 6, the horseshoe shaped protrusion (210) of the hard cover cutter (200) is positioned between the hard cover (140) and the adhesive tape (130). When the hard cover cutter (200) is pushed by the hands of the operator, the protrusion (210) easily slides on the smooth surface of the adhesive tape (130), and thereby the cutting tool (220) installed in the hard cover cutter (200) is moved and allows the hard cover (140) to be easily cut.

The cast cutter according to the present invention prevents shock or injury to the patient when the cast is removed from the affected area and therefore, the operator of the cast cutter does not need to work slowly and need not be overlyfocused on the patient and thereby the cast may be removed from the affected area in a shorter amount of time.

In addition, the cast cutter of this invention is able to collect dust and debris generated when removing the cast from the affected area and therefore does not discomfort the patient.

In addition, conventionally, the cut cast needed to be removed from the affected area by a separate device, but the cast cutter of this invention allows the cast removal to be done quickly and easily and therefore the cutting operation may be done twice along spaced portions and in turn, does not require a separate device to spread the cut cast open.

In addition, by applying a cast according to the method of this invention, the cast is applied in such a manner so that the horseshoe-shaped protrusion mounted on the hard cover cutter of this invention does not get caught in the cast padding during cast removal operations and thereby the hard cover may be cut quickly and the cast may be removed swiftly.

What is claimed is:

1. A surgical cast cutter comprising:
   a first housing extending in the longitudinal direction, having an opening at the bottom of the front end which is closed by a stop plate, a motor having a front axle extending to the front end of said first housing, a transmission connected to said front axle and which changes the speed of a first output axle, which is parallel to said front axle, to predetermined revolutions, a second output axle which is perpendicular to said first output axle and passes through said opening, a set of bevel gears which converts rotation centered on said first output axle to rotation centered on said second output axle and which is provided with an integrated cylindrical portion on the output side, and a third output axle which is connected to said cylindrical portion in a key connection manner;
   a second housing including a built-in cutting tool which is comprised of a first shank, a cutting portion, and a second shank and connected to said third output axle in a key connection manner with interposed bearings on each of said first and second shank, and a protrusion comprised of a first portion extending parallel to said cutting tool and a second portion which is integrated with the front end of said first portion and extends from the front end of said first portion in a perpendicular direction to the cutting tool and having a second aperture formed thereon;
   a cascaded first joint to which said stop plate is coupled on the top and which the bottom thereof is joined to the said second housing having threaded portions on the top outer circumference, and through which the first shank of said cutting tool is passed;
   a second joint of which the top thereof is coupled to said stop plate and which the bottom thereof having a shape corresponding to the cascaded shape of said first joint in the inner circumference and receiving said first joint;
   a hood having a threaded aperture formed on the top portion perpendicular to the cutting tool, an L shaped nipple-type connector formed on one side, and coupled by a bolt to the second housing on which a slot shaped groove is formed on a position corresponding to said aperture and parallel to said cutting tool; and
   a spring interposed between said second joint and said hood.

2. The surgical cast cutter of claim 1, wherein said hood is transparent.

3. The surgical cast cutter of claim 1, wherein the outer surface of said hood is a smooth surface.

4. The surgical cast cutter of claim 1, wherein all edges of said hood are rounded.

5. The surgical cast cutter of claim 1, wherein a display which indicates the cast cutting direction is formed on the distal end surface of said hood.

6. The surgical cast cutter of claim 1, wherein said second portion is plate shaped, and the thickness thereof decreases from the proximal end to the distal end, and from the center portion to both ends.

* * * * *